(12) United States Patent
Uhm et al.

(10) Patent No.: US 6,440,721 B2
(45) Date of Patent: *Aug. 27, 2002

(54) METHOD FOR PREPARING AN R- OR S-FORM OF α-SUBSTITUTED HETEROCYCLIC CARBOXYLIC ACID AND A COUNTER ENANTIOMERIC FORM OF α-SUBSTITUTED HETEROCYCLIC CARBOXYLIC ACID ESTER THERETO USING ENZYME

(75) Inventors: Ki-Nam Uhm; Sang-Chul Lim; Jong-Ho Lim, all of Taejon (KR)

(73) Assignee: SK Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/870,209

(22) Filed: May 30, 2001

(30) Foreign Application Priority Data

Jun. 1, 2000 (KR) .............................. 00-30073

(51) Int. Cl.$^7$ ................................................. C07C 7/00
(52) U.S. Cl. ....................................................... 435/280
(58) Field of Search ........................................ 435/280

(56) References Cited

U.S. PATENT DOCUMENTS 5,928,933 A   7/1999   Dicosimo et al. ........... 435/280

FOREIGN PATENT DOCUMENTS

JP      1216983      8/1989
JP       971576      3/1997

*Primary Examiner*—Sandra E. Saucier
*Assistant Examiner*—Vera Afremova
(74) *Attorney, Agent, or Firm*—Abelman, Frayne & Schwab

(57) ABSTRACT

Disclosed is a method for preparing an R- or S-forms of α-substituted heterocyclic carboxylic acid (α-HCCA) and a counter enantiomeric form of α-substituted heterocyclic carboxylic acid ester thereto by use of an enzyme. A racemic α-HCCA is reacted with alcohol to give a racemic α-HCCA ester, which is then brought into contact with an enzyme with enantioselectivity, whereby either R-form or S-form of the racemate is hydrolyzed. Extraction with an organic solvent can obtain enantiomers of the α-HCCA ester. Thus, a certain enantiomeric form of α-HCCA and a counter enantiomeric form of α-HCCA ester thereto, respectively can be prepared with high optical purity at high yields as well as at low cost.

6 Claims, No Drawings

METHOD FOR PREPARING AN R- OR S-FORM OF α-SUBSTITUTED HETEROCYCLIC CARBOXYLIC ACID AND A COUNTER ENANTIOMERIC FORM OF α-SUBSTITUTED HETEROCYCLIC CARBOXYLIC ACID ESTER THERETO USING ENZYME

BACKGROUND OF THE INVENTION

1. Field of the Invention

The present invention relates to a method for preparing an R- or S-form α-substituted heterocyclic carboxylic acid (hereinafter referred to as "α-HCCA") and a counter enantiomeric form of α-HCCA ester. More particularly, the present invention pertains to a method for preparing R- or S-form α-HCCA and S- or R-form α-HCCA ester, respectively using an enzyme catalyst with enantioselectivity from a racemate of α-HCCA ester obtained by reacting a racemic α-HCCA and alcohol.

2. Description of the Prior Art

Divided into optical isomers, R- and S-form, tetrahydro-2-furoic acid (hereinafter referred to as "THFA"), a kind of α-HCCA, is an important chiral building block which has various applications in chemistry. Of the optical isomers, R-(+)-THFA is used as a side chain intermediate for the synthesis of penem type antibiotics while S-(−)-THFA is useful as a chiral intermediate for organic synthesis. Thus, THFA is different in use from R form to S form. However, because THFA is obtained in the form of racemate when chemically synthesized, additional processes are required to separate THFA into enantiomers thereof: R and S forms.

Optical resolution has been usually used to divide racemic THFA into R- and S-forms thereof. In 1983, Belanger successfully separated THFA racemate into enantiomers thereof by use of brucine and ephedrine as resolving agents (Can. J. Chem., 61, 1383 (1983)). However, the resolving agents are not economical because of their being very expensive. Another problem with this process is low in enantiomeric excess value.

Japanese Pat. Laid-Open Publication No. 89-216983 discloses the use of a chiral amine(1-(4-halogenophenyl)ethylamine) as a resolving agent, in which diastereomer salts are prepared from R,S-THFA and optically resolved. This method is also economically unfavorable owing to the high price of the chiral amine. Additionally, only low production yields can be obtained because the amount of R,S-THFA to be added in the early reaction is limited to as low as 4 mmol. Furthermore, the chiral THFA finally obtained is poor in enantiomeric excess value.

Japanese Pat. Laid-Open Publication. No. 97-71576 refers to a method of synthesizing R- or S-THFA by treating R- or S-THFA salts with hydrogen halide, which is different from optical resolving methods.

It has been well known for some time that racemates could be optically resolved using enzyme catalysts, such as esterases, lipases, and proteases, to enantioselectively hydrolyze one of the two enantiomers present. For example, U.S. Pat. No. 5,928,933 discloses an enzyme with an enantiomeric excess value of 95% as a result of extensive experiments for reaction specificity of 44 enzymes, including proteases, lipases and esterases. The enzyme catalyst is very useful for the separation of enantiomeric racemates, but because the selectivity for enantiomers and the optical purity of products may vary depending on the choice of enzyme and the chemical structures of substrates, intensive efforts are required to find combinations of enzymes suitable for substrates. Especially, nowhere is found a method for optical resolution of α-HCCA using an enzyme.

SUMMARY OF THE INVENTION

Leading to the present invention, the intensive and through research on the optical resolution of α-HCCA, conducted by the present inventors aiming to develop an optically highly pure α-HCCA and a counter enantiomeric form of α-HCCA ester thereto by an economical procedure, resulted in the finding that some of microorganism- or animal-derived hydrolyzing enzymes may enantioselectively hydrolyze the ester functionality of particular optical isomers of α-HCCA esters at high efficiency.

Therefore, it is an object of the present invention to overcome the above problems encountered in prior arts and to provide a method for preparing a highly pure R- or S-form α-HCCA and a counter enantiomeric form of α-HCCA ester thereto using an enzyme, which is economically favorable.

Based on the present invention the above object could be accomplished by providing a method for preparing an R- or S-form α-HCCA and a counter enantiomeric form of α-HCCA ester thereto, comprising the steps of:

reacting a racemic α-HCCA with alcohol to give a racemic α-HCCA ester represented by the following chemical formula 1:

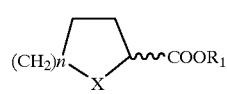

1 wherein $R_1$ is selected from the group consisting of substituted or unsubstituted alkyl or alkenyl containing 1 to 6 carbon atoms, benzyl, cycloalkyl containing 3 to 6 carbon atoms, substituted or unsubstituted arylalkyl, and substituted or unsubstituted heteroarylalkyl, X represents O, S or N—H, and n is an integer of 1 to 3;

optically resolving the racemate of the formula 1 by use of an enzyme with enantioselectivity to hydrolyze either R-form or S-form of the racemate, thereby producing a pure R-form or S-form of α-HCCA and a counter enantiomeric form of α-HCCA ester thereto, said enzyme existing as a powder or an aqueous solution; and extracting the unhydrolyzed α-HCCA ester with an organic solvent.

DETAILED DESCRIPTION OF THE INVENTION

The present invention is characterized by the enantioselective hydrolysis of esters of racemic α-HCCA by an enzyme to produce a certain enantiomeric form of α-HCCA and a counter enantiomeric form of the esters of α-HCCA, at once. The separation of the hydrolyzed α-HCCA and the remaining esters of α-HCCA can be achieved by extracting with an organic solvent.

In detail, α-HCCA is reacted with an alcohol at an equivalent amount to produce an α-HCCA ester, which is then enantioselectively hydrolyzed at a constant temperature and pH in an aqueous solution in the presence of an enzyme with enantioselectivity. As a result, the reaction produces an R- or S-form α-HCCA, along with the ester of α-HCCA which has an enantiomeric form counter to that of the hydrolyzed α-HCCA. After the completion of the enantioselective hydrolysis, addition of an organic solvent extracts the ester of α-HCCA thereinto, leaving the α-HCCA in the aqueous phase only. Removal of the organic solvent from the organic phase results in acquisition of an optically pure S- or R-form of α-HCCA ester. Poor in optical purity, the α-HCCA remaining in the aqueous solution may be increased in purity through a purification process using, for example, a column, or may be reused as a starting material in the present invention.

Using a non-enantioselective enzyme or a palladium catalyst, the S- or R-form of α-HCCA ester obtained can be hydrolyzed to an S- or R-form of α-HCCA with a high enantiomeric excess value (>99%). Additionally, the S- or R-form of α-HCCA ester may be reduced to a chiral alcohol which is useful as an intermediate for the synthesis of various medicines.

For instance, the enantiomeric α-HCCA ester is hydrolyzed at a constant pH and temperature in an aqueous solution in the presence of an enzyme that shows no enantioselectivity and non-specifically hydrolyzes α-HCCA ester. After completion of the enzymatic hydrolysis, the aqueous layer is controlled to pH 2–3 with hydrochloric acid and extracted several times with an organic solvent to yield an S- or R-form of α-HCCA. In the case of an palladium catalyst (Pd/C), the obtained S- or R-form of α-HCCA ester is dissolved in an organic solvent and subjected to hydrogenation at a constant temperature under a predetermined partial hydrogen pressure to produce an S- or R-form of α-HCCA with a high optical purity (>99%).

In accordance with a preferred embodiment of the present invention, THFA, which belongs to an α-HCCA, is reacted with alcohol at an equivalent amount to give a THFA ester adduct which is then subjected to optical resolution in the presence of an enantioselectively hydrolyzing enzyme to afford an R- or S-form of THFA while leaving a counter enantiomeric form of the THFA ester, which is extracted with an organic solvent. Using a non-enantioselective enzyme or a palladium catalyst, this enantiomeric THFA ester can be returned to an enantiomeric form of THFA with a high optical purity (>99%). Aside from THFA, all materials falling within the scope of α-HCCA, for example, proline and tetrahydrothiopen-2-carboxylic acid can be optically resolved in accordance with the present invention.

Useful in the present invention are linear or branched alcohols containing 1–6 carbon atoms, aromatic alcohols, cycloalkyl alcohols containing 3–6 carbon atoms, substituted or unsubstituted arylalkyl alcohols, and substituted or unsubstituted heteroarylalkyl alcohols. Preferred are linear alcohols containing 4 or more carbon atoms or aromatic alcohols, when consideration is taken of reaction time and optical purity.

For use in the enantioselective hydrolysis of α-HCCA ester, the enzyme is preferably selected from the group consisting of lipases, proteases, and esterases, all of which are derived from microorganisms or animals. Depending on enzymes, the conformation of the α-HCCA hydrolyzed is determined. Such an enantioselective enzyme, when used, may be in a form of a powder or an aqueous solution. The enzyme is preferably used in an amount of 0.1 to 100 parts by weight based on 100 parts by weight of the α-HCCA ester. For example, if the enzyme amount is less than 0.1 part by weight, the hydrolysis may require excessive time to complete. On the other hand, an enzyme amount exceeding 100 parts by weight increases the production cost.

The enzymatic reaction is optimally carried out at 0–60° C. and pH 4–12. As for the organic solvent to extract the remaining enantiomeric α-HCCA ester, it is preferably selected from the group consisting of ethyl acetate, dichloromethane, chloroform, carbon tetrachloride, toluene and mixtures thereof.

Turning now to the reduction of the prepared enantiomeric α-HCCA ester to a corresponding conformation of α-HCCA, a palladium catalyst is preferably used in an amount of 0.1 to 30% by weight and more preferably in an amount of 0.5 to 10% by weight. For example, an amount less than 0.1% by weight is insufficient to perform the hydrogenation. On the other hand, an amount larger than 30% by weight has negative influence on the production cost. At this time, the catalytic hydrogenation of the enantiomeric α-HCCA ester is preferably carried out at a hydrogen partial pressure of 1 to 10 Bars and more preferably at a hydrogen partial pressure of 1 to 5 Bars. For example, the hydrogenation, when being carried out at a hydrogen partial pressure less than 1 bar, is significantly deteriorated in efficiency. On the other hand, a hydrogen partial pressure larger than 10 Bars results in a lot of side products. Other conditions are set at 1 to 20 hours and preferably at 1 to 8 hours for reaction time and at 0 to 70° C. and preferably at 20 to 40° C. for reaction temperature.

A better understanding of the present invention may be obtained in light of the following examples which are set forth to illustrate, but are not to be construed to limit the present invention.

EXAMPLE 1

Screening of Enzyme for Specificity for THFA Ethyl Ester

After being well mixed, 0.1 mole of THFA and 0.3 mole of ethyl alcohol were reacted at 70° C. for 1 hour in the presence of 0.15 mole of thionyl chloride to produce THFA ethyl ester.

To 500 μl of a 50 mM phosphate buffer (pH 7.0), THFA ethyl ester and a hydrolyzing enzyme were added at amounts of 1% and 0.1%, respectively and the resulting reaction was incubated at 30° C. for 30 hours. After completion of the hydrolysis, 50 μl of the reaction was well mixed with an equal volume of 1 N HCl and added with 200 μl of ethyl acetate to extract the remaining substrate. The extract was analyzed by gas chromatography (GC) on a HP-5 column at a temperature range from 80 to 200° C. and by chiral gas chromatography (GC) on a β-dextrin GC column at a temperature range from 110 to 200° C.

Analysis results are summarized in Table 1, below. As seen in Table 1, the remaining THFA ethyl ester existed as either an R-form, an S-form or a racemate, depending on the enantioselectivity of the enzymes. Therefore, it is confirmed that different enantiomers of THFA ethyl ester can be prepared according to the choice of enzyme.

TABLE 1

| Enzyme | | Optical Purity (ee%)[1] | | Chiral Form (THFA Ethyl | |
|---|---|---|---|---|---|
| Kind | Source | THFA-C2 | THFA | (Ester) | Note |
| Protease | Papain | | | | Unreacted |
| | Bacillus subtilis | 27.7% | 51.2% | S | |
| | Aspergillus oryzae | 30.1% | 22.3% | S | |
| | Aspergillus saitoi | | | | Unreacted |
| | Rhizopus. sp | | | | |
| | Bacillus licheniformis | 26% | 13.2% | S | Unreacted |
| | Bacillus amyloliquefaciens | 0% | | | |
| Lipase | Candida cylindracea | 88% | 12.3% | | |
| | Aspergillus oryzae | 15.4% | 5.6% | R | |
| | Fongipase | 12.2% | 9.3% | R | |
| | Pseudomonas sp. (immobilized) | 35.3% | 5.7% | S | |
| | Pseudomonas sp. | 3.1% | 0.2% | R | |
| | Candida sp. | 21.5% | 2.5% | R | |
| | Procine pancreatic | 93.1% | 19.8% | S | |
| | Candida antartica, fraction B | | | | |
| | Novo IM lipase | 6.2% | 2.5% | R | |
| | Candida rugosa | 0% | | | |
| | Rhizomucor miehei | 13.5% | 1.1% | R | |
| | K80 lipase | 7.6% | 8.2% | S | |
| | L1 lipase | | | | Unreacted |
| | L62 lipase | 16.9% | 10.5% | S | |
| Esterase | Procine liver | 0% | | | Unreacted |

[1] $ee\% = \dfrac{R - S}{R + S} \times 100$ wherein R and S mean total molar concentrations of R-form and S-form enantiomers, respectively.

EXAMPLE 2

Screening of Enzyme for Specificity for THFA Butyl Ester 0.1 mole of THFA was reacted with 0.1 mole of butyl alcohol at 120° C. for 4 hours in 0.15 mole of toluene in the presence of 1×10$^{-4}$ mole of p-toluenesulfonic acid to produce THFA butyl ester.

To 500 μl of a 50 mM phosphate buffer (pH 7.0), THFA ethyl ester and a hydrolyzing enzyme were added at amounts of 1% and 0.1%, respectively and the resulting reaction was incubated at 30° C. for 16 hours. After completion of the hydrolysis, the substrate was extracted and analyzed in the same manner as in Example 1.

Analysis results are summarized in Table 2, below. As apparent from data of Table 2, the remaining α-HCCA ethyl ester existed as either an R-form, an S-form or a racemate, depending on the enantioselectivity of the enzymes. Therefore, it is confirmed that different enantiomers of THFA ethyl ester can be prepared according to the choice of enzyme.

TABLE 2

| Enzyme | | Optical Purity (ee%)[1] | | Chiral Form (THFA Butyl | |
|---|---|---|---|---|---|
| Kind | Source | THFA-C4 | THFA | Ester) | Note |
| Protease | Papain | | | | Unreacted |
| | Bacillus subtilis | 16.8% | 37.8% | S | |
| | Aspergillus niger | 100% | 40.5% | R | |
| | Aspergillus oryzae | 100% | 24.6% | S | |
| | Aspergillus saitoi | 5.6% | 27.8% | R | Weakly reacted |
| | Rhizopus. sp | | | | Unreacted |
| | Bacillus licheniformis | 100% | 29.8% | S | |
| | Bacillus amyloliquefaciens | | | | Unreacted |
| Lipase | Candida cylindracea | 88% | 12.3% | R | |
| | Aspergillus oryzae | 79.3% | 0.6% | R | |
| | Fongipase | 76.15% | 2.7% | R | |
| | Pseudomonas sp. (immobilized) | 35.3% | 5.7% | S | |
| | Pseudomonas sp. | 19.1% | 3.7% | S | |
| | Candida sp. | 65.8% | 14.1% | R | |
| | Porcine pancreatic | 35.7% | 20.3% | S | |
| | Candida antartica, fraction B | 16.1% | 11.3% | R | |

TABLE 2-continued

| Enzyme | | Optical Purity (ee%)[1] | | Chiral Form (THFA Butyl Ester) | Note |
|---|---|---|---|---|---|
| Kind | Source | THFA-C4 | THFA | | |
| | Novo IM lipase | 100% | 2.96% | R | |
| | Candida rugosa | 81% | 6% | R | |
| | Rhizomucor miehei | | | | Unreacted |
| | K80 lipase | 51.4% | 11% | S | |
| | L1 lipase | 47.1% | 16.3% | R | |
| | L62 lipase | 81.5% | 8.4% | S | |
| Esterase | Porcine liver | 42.2% | 25.3% | R | |

[1] $ee\% = \dfrac{R - S}{R + S} \times 100$ wherein R and S mean total molar concentrations of R-form and S-form enantiomers, respectively.

EXAMPLE 3

Screening of Enzyme for Specificity for THFA Benzyl Ester

THFA benzyl ester was prepared in a manner similar to that of Example 1, except that benzyl alcohol was used.

To 500 µl of a 50 mM phosphate buffer (pH 7.0), THFA benzyl ester and a hydrolyzing enzyme were added at amounts of 1% and 0.1%, respectively and the resulting reaction was incubated at 30° C. for 16 hours. After completion of the hydrolysis, the substrate was extracted and analyzed in the same manner as in Example 1.

Analysis results are summarized in Table 3, below. As apparent from data of Table 3, the remaining α-HCCA benzyl ester existed as either an R-form, an S-form or a racemate, depending on the enantioselectivity of the enzymes. Therefore, it is confirmed that different enantiomers of THFA ethyl ester can be prepared according to the choice of enzyme.

TABLE 3

| Enzyme | | Optical Purity (ee%)[1] | | Chiral Form (THFA-Benzyl Ester) | Note |
|---|---|---|---|---|---|
| Kind | Source | THFA-Bz | THFA | | |
| Protease | Papain | | | | Unreacted |
| | Bacillus subtilis | 94.7% | 31.8% | S | |
| | Aspergillus oryzae | 98.3% | 26.5% | S | |
| | Aspergillus saitoi | 22.2% | 19.9% | S | |
| | Rhizopus.sp | 38.4% | 44.1% | S | |
| | Bacillus licheniformis | 91.5% | 29.1% | S | |
| | Bacillus amyloliquefaciens | 83.6% | 36% | S | |
| Lipase | Candida cylindracea | 0.7% | 5.8% | — | |
| | Aspergillus oryzae | 18.1% | 22% | R | |
| | Fongipase | 0% | | | |
| | Pseudomonas sp. (immobilized) | 13.1% | 21.9% | S | |
| | Pseudomonas sp. | 1.8% | 9.5% | S | |
| | Candida sp. | 0% | | | |
| | Porcine pancreatic | 0% | | | |
| | Candida antartica, fraction B | 35% | 10.7% | S | |
| | Novo IM lipase | 78.3% | 3.9% | R | |
| | Candida rugosa | 0% | | | |
| | Rhizomucor miehei | 0% | | | |
| | K80 lipase | 92.1% | 20.4% | S | |
| | L1 lipase | 40% | 6% | R | |
| | L62 lipase | 0% | | | |
| Esterase | Porcine liver | 0% | | | |

[1] $ee\% = \dfrac{R - S}{R + S} \times 100$ wherein R and S mean total molar concentrations of R-form and S-form enantiomers, respectively.

EXAMPLE 4

Separation of THFA Ester and THFA Using Organic Solvent

Racemic THFA ester was enantioselectively hydrolyzed by an enzyme and an organic solvent was added to the enzyme reaction to separate the R- or S-form of the product THFA from the corresponding S- or R-form of the substrate remaining unhydrolyzed as follows.

To 1 liter of a 50 mM phosphate buffer (pH 7.0), R, S-THFA butyl ester and Bacillus licheniformis protease were added at amounts of 2% and 1%, respectively and the resulting reaction was incubated at 30° C. for 4 hours under a condition of pH 7. After completion of the hydrolysis, the substrate was extracted and analyzed in the same manner as in Example 1.

The remainder of the reaction was added with 500 ml of ethyl acetate and mixed well, followed by phase separation to recover the organic layer. The aqueous layer was extracted one more time with 500 ml of ethyl acetate and the ethyl acetate layers obtained were pooled. This pooled organic layer was dehydrated over 5 g of sodium sulfate. Vacuum distillation removed the ethyl acetate, leaving 9.6 g of S-THFA butyl ester which was measured to be 99.4% in enantiomeric excess. The THFA remaining in the aqueous phase was identified to be an R-form with 70% enantiomeric excess.

EXAMPLES 5 TO 13
Change in Enantiomeric Excess According to Ratio of Enzyme: Substrate, Temperature and pH The same procedure as in Example 4 was conducted, except that the concentration of R, S-THFA butyl ester was fixed at 8% by weight while varying the ratio of enzyme:substrate, reaction temperature, and pH. Results are given in Table 4, below.

TABLE 4

| Example No. | Enz.:Sub | Rxn Time (hr) | Rxn Temp. (° C.) | Optical Purity (ee %) | pH |
|---|---|---|---|---|---|
| 5 | 1:2 | 5 | 50 | 100 | inconstant |
| 6 | 1:2 | 2 | 50 | 98.6 | 7 |
| 7 | 1:4 | 3.5 | 50 | 98.4 | 7 |
| 8 | 1:8 | 7.5 | 50 | 98.9 | 7 |
| 9 | 1:4 | 4 | 50 | 98.6 | 9 |
| 10 | 1:8 | 4 | 50 | 98.5 | 9 |
| 11 | 1:8 | 4 | 30 | 98.7 | 9 |
| 12 | 1:12 | 8.5 | 30 | 98.8 | 9 |
| 13 | 1:16 | 11 | 30 | 97.4 | 9 |

EXAMPLE 14
Optical Resolution of Butyl Ester Using *Bacillus licheniformis* Protease To 400 ml of a 50 mM phosphate buffer (pH 9.0) were added 12% by weight of R, S-THFA butyl ester and 1% by weight of *Bacillus licheniformis* protease and the resulting reaction was incubated at 30° C. for 10.5 hours with maintenance of pH 9.0. After completion of the hydrolysis, the was extracted and analyzed in the same manner as in Example 1.

Using 200 ml of ethyl acetate, 21 g of S-THFA butyl ester was obtained in the same manner as in Example 4, and analyzed to be 99.3% in enantiomeric excess. The THFA remaining in the aqueous phase was identified to be an R-form with 60% enantiomeric excess.

EXAMPLE 15
Optical Resolution of Butyl Ester Using *Bacillus licheniformis* Protease 12 g of S-THFA butyl ester was prepared in a manner similar to that of Example 14, except that 200 ml of a 50 mM phosphate buffer (pH 9.0) was used at 20° C. for the hydrolysis and 100 ml of ethyl acetate was added for substrate separation, and its optical purity was measured to be 99.3% enantiomeric excess.

EXAMPLE 16
Optical Resolution of Butyl Ester Using *Bacillus licheniformis* Protease 21 g of S-THFA butyl ester was prepared in a manner similar to that of Example 14, except that the hydrolysis was carried out at 10° C. for 19 hours, and its optical purity was measured to be 99.1% in enantiomeric excess.

EXAMPLE 17
Optical Resolution of Butyl Ester Using *Bacillus licheniformis* Protease 25.7 g of S-THFA butyl ester was prepared in a manner similar to that of Example 14, except that the hydrolysis was carried out at 20° C. for 26 hours with 15% by weight of R, S-THFA butyl ester in 200 ml of a 50 mM phosphate buffer (pH 9.0) and 100 ml of ethyl acetate was added for substrate separation, and its optical purity was measured to be 99.8% in enantiomeric excess.

EXAMPLES 18 TO 22
Optical Resolution of Butyl Ester Using *Bacillus licheniformis* Protease S-THFA butyl ester was prepared under the same conditions as in Example 17 while varying concentrations of R, S-THFA butyl ester and the ratio of enzyme to substrate according to the instructions of Table 5, below. Analysis results are also given in Table 5.

TABLE 5

| Example No. | Sub. Conc. | Enz.:Sub | Rxn Time (hr) | Yield (%) | ee % |
|---|---|---|---|---|---|
| 18 | 15% | 1:12 | 21 | 25.5 | 100 |
| 19 | 30% | 1:12 | 24 | 30 | 99 |
| 20 | 30% | 1:15 | 26 | 33.7 | 99.2 |
| 21 | 40% | 1:15 | 28 | 46.4 | 99.1 |
| 22 | 50% | 1:12 | 30 | 50 | 98.9 |

EXAMPLE 23
Preparation of S-THFA from S-THFA Butyl Ester

In the presence of *Candida antarctica*, fraction B lipase, which was demonstrated to non-enantioselectively hydrolyze R, S-THFA butyl ester in Example 2, S-THFA butyl ester was hydrolyzed to S-THFA without using strong acid and strong base nor producing isomers.

To 300 ml of a 50 mM phosphate buffer (pH 7.0) were added 1% by weight of S-THFA butyl ester and 0.1% by weight of *Candida antarctica*, fraction B lipase and the resulting reaction was incubated at 30° C. for 1 hour. After completion of the hydrolysis, the substrate was extracted and analyzed in the same manner as in Example 1.

GC analysis confirmed the hydrolysis of all S-THFA butyl ester to THFA which was found to be 99.8% in enantiomeric excess as measured by chiral GC.

EXAMPLES 24 TO 32
Preparation of S-THFA from S-THFA Butyl Ester

The procedure of Example 23 was carried out using different enzymes, and the results are given in Table 6, below.

TABLE 6

| Example No. | Enzyme | Rxn Time (hr) | ee % (S-THFA) |
|---|---|---|---|
| 24 | *Aspergillus oryzae* lipase | 16 | 100 |
| 25 | Fongipase | 16 | 100 |
| 26 | Pseudomonas sp. Lipase (immobilized) | 16 | 100 |
| 27 | Pseudomonas sp. Lipase | 16 | 100 |
| 28 | Candida sp. Lipase | 1.5 | 100 |
| 29 | *Candida antarctica*, fraction B Lipase | 1 | 100 |

TABLE 6-continued

| Example No. | Enzyme | Rxn Time (hr) | ee % (S-THFA) |
|---|---|---|---|
| 30 | Novo IM Lipase | 5 | 100 |
| 31 | L62 lipase | 2.5 | 100 |
| 32 | Porcine liver Esterase | 0.15 | 100 |

EXAMPLE 33

Optical Resolution of THFA

To 200 ml of a 50 mM phosphate buffer (pH 9.0) were added 12% by weight of R, S-THFA butyl ester and 1% by weight of *Bacillus licheniformis* protease and the resulting reaction was incubated at 30° C. for 10.5 hours with maintenance of pH 9.0. After the hydrolysis, the reaction was analyzed as in Example 1. After the remainder of the reaction was added with 100 ml of ethyl acetate and mixed well, 12 g of S-THFA butyl ester was obtained in the same manner as in Example 14 and identified to be 99.3% in enantiomeric excess.

In 100 ml of a 50 mM phosphate buffer (pH 7.0), 12 g of the prepared S-THFA butyl ester was hydrolyzed at 30° C. for 5 hours in the presence of 1 g of *Candida antarctica*, fraction B lipase with maintenance of pH 7.0. Following the hydrolysis, the reaction results were analyzed as in Example 1. The remainder of the reaction was adjusted to pH 2.0 with HCl, followed by three extractions with 3 volumes of ethyl acetate. After the ethyl acetate extracts were pooled, 6 g of S-THFA was recovered from the pool in the same manner as in Example 14. The compound was found to be 99.3% in enantiomeric excess as measured by chiral GC.

EXAMPLE 34

Mass-Scale Optical Resolution of THFA

To 2 liters of a 50 mM phosphate buffer (pH 9.0) were added 40% by weight of R, S-THFA butyl ester and 3% by weight of *Bacillus licheniformis* protease and the resulting reaction was incubated at 30° C. for 23 hours with maintenance of pH 9.0. After the hydrolysis, the reaction was analyzed as in Example 1. After the remainder of the reaction was added with 1 liter of ethyl acetate and mixed well, 400 g of S-THFA butyl ester was obtained in the same manner as in Example 14 and identified to be 99.3% in enantiomeric excess.

In 400 ml of a 50 mM phosphate buffer (pH 7.0), 160 g of the prepared S-THFA butyl ester was hydrolyzed at 30° C. for 6 hours in the presence of 8 g of *Candida antarctica*, fraction B lipase with maintenance of pH 7.0. Following the hydrolysis, the reaction results were analyzed as in Example 1. The remainder of the reaction was adjusted to pH 2.0 with HCl, followed by three extractions with 3 volumes of ethyl acetate. After the ethyl acetate extracts were pooled, 80 g of S-THFA was recovered from the pool in the same manner as in Example 14. The compound was found to be 99.3% in enantiomeric excess as measured by chiral GC.

EXAMPLE 35

Optical Resolution of THFA

A butyl ester racemate was prepared in the same manner as in Example 3. To 200 ml of a 50 mM phosphate buffer (pH 9.0) were added 12% by weight of the prepared R, S-THFA butyl ester and 1% by weight of *Bacillus licheniformis* protease and the resulting reaction was incubated at 20° C. for 4.5 hours with maintenance of pH 9.0. After completion of the hydrolysis, the reaction was analyzed as in Example 1. The remainder of the reaction was added with 100 ml of ethyl acetate and mixed well, after which 16 g of S-THFA butyl ester was obtained in the same manner as in Example 14 and identified to be 99.1% in enantiomeric excess.

In 20 ml of ethyl acetate was dissolved 55 g of the obtained S-THFA benzyl ester and added 55 mg (1% by weight) of 10% palladium catalyst (Pd/C), followed by stirring the solution at room temperature for 10 min. Hydrogen gas was fed into the reaction little by little to a hydrogen partial pressure of 1.5 Bars at which point stirring was resumed for 10 hours. After removal of the palladium catalyst through filtration, vacuum distillation of the ethyl acetate and produced toluene left 2.5 g of S-THFA. This enantiomeric compound was found to be 99.1% in enantiomeric excess as measured by chiral GC.

As described hereinafter, α-HCCA and ester thereof can be prepared as enantiomeric compounds with high optical purity at high yields in accordance with the present invention. Additionally, the present invention is economically favorable because such chiral compounds can be produced at low cost.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing an R- or S-form α-substituted heterocyclic carboxylic acid and a counter enantiomeric form of α-substituted heterocyclic carboxylic acid ester thereto, comprising the steps of:

reacting a racemic α-substituted heterocyclic carboxylic acid with alcohol to give a racemic α-substituted heterocyclic carboxylic acid ester having the following chemical formula 1:

1 wherein, $R_1$ is selected from the group consisting of substituted or unsubstituted alkyl or alkenyl containing 1 to 6 carbon atoms, benzyl, cycloalkyl containing 3 to 6 carbon atoms, substituted or unsubstituted arylalkyl, and substituted or unsubstituted heteroarylalkyl, X represents O, S or NH, and n is an integer of 1 to 3;

optically resolving the racemate of the formula 1 in an aqueous solution by use of an enzyme with enantioselectivity to hydrolyze either R-form or S-form of the racemate, thereby producing an R-form or S-form of α-substituted heterocyclic carboxylic acid and a counter enantiomeric form of α-substituted heterocyclic carboxylic acid ester thereto, said enzyme existing as a powder or an aqueous solution;

extracting the unhydrolyzed α-substituted heterocyclic carboxylic acid ester of the racemate with an organic solvent, followed by recovering the α-substituted heterocyclic carboxylic acid ester from the organic phase and the α-substituted heterocyclic carboxylic acid from the aqueous phase, respectively; and subjecting the recovered α-substituted heterocyclic carboxylic acid ester in an organic solvent to hydrogenation under a constant hydrogen partial pressure at a constant temperature in the presence of a palladium catalyst on carbon (Pd/C), followed by recovering the resulting α-substituted heterocyclic carboxylic acid.

2. The method set forth in claim 1, wherein said alcohol is selected from the group consisting of linear or branched alcohols containing 1 to 6 carbon atoms, aromatic alcohols, cycloalkyl alcohols containing 3 to 6 carbon atoms, substituted or unsubstituted arylalkyl alcohols, and substituted or unsubstituted heteroarylalkyl alcohols.

3. The method as set forth in claim 1, wherein said enzyme is derived from microorganisms or animals and selected from the group consisting of lipases, proteases and esterases.

4. The method as set forth in claim 1, wherein said enzyme is used in an amount of 0.1 to 100 parts by weight based on 100 parts by weight of α-substituted heterocyclic carboxylic acid ester.

5. The method as set forth in claim 1, wherein said optical resolving step is carried out in an aqueous solution at 0 to 60° C. with maintenance of pH at 4 to 12.

6. The method as set forth in claim 1, wherein said organic solvent is selected from the group consisting of ethyl acetate, dichloromethane, chloroform, carbon tetrachloride, toluene, and mixtures thereof.

* * * * *

UNITED STATES PATENT AND TRADEMARK OFFICE
CERTIFICATE OF CORRECTION

PATENT NO.   : 6,440,721 B2
DATED        : August 27, 2002
INVENTOR(S)  : Uhm et al.

It is certified that error appears in the above-identified patent and that said Letters Patent is hereby corrected as shown below:

<u>Column 12, line 30 to Column 13, line 4,</u>
Claim 1, should read:

1. A method for preparing an R- or S-form α-substituted heterocyclic carboxylic acid and a counter enantiomeric form of α-substituted heterocyclic carboxylic acid ester thereto, comprising the steps of:
    reacting a racemic α-substituted heterocyclic carboxylic acid with alcohol to give a racemic α-substituted heterocyclic carboxylic acid ester having the following chemical formula 1:

1 - wherein:
   $R_1$ is selected from the group consisting of substituted or unsubstituted alkyl or alkenyl containing 1 to 6 carbon atoms, benzyl, cycloalkyl containing 3 to 6 carbon atoms, substituted or unsubstituted arylalkyl, and substituted or unsubstituted heteroarylalkyl, X represents O, S or NH, and n is an integer of 1 to 3;

optically resolving the racemate of the formula 1 in an aqueous solution by use of an enzyme with enantioselectivity to hydrolyze either R-form or S-form of the racemate, thereby producing an R-form or S-form of α-substituted heterocyclic carboxylic acid and a counter enantiomeric form of α-substituted heterocyclic carboxylic acid ester thereto, said enzyme existing as a powder or an aqueous solution;

UNITED STATES PATENT AND TRADEMARK OFFICE
CERTIFICATE OF CORRECTION

PATENT NO. : 6,440,721 B2
DATED : August 27, 2002
INVENTOR(S) : Uhm et al.

It is certified that error appears in the above-identified patent and that said Letters Patent is hereby corrected as shown below:

<u>Column 12, line 30 to Column 13, line 4, cont'd,</u>
  extracting the unhydrolyzed α-substituted heterocyclic carboxylic acid ester of the racemate with an organic solvent, followed by recovering the α-substituted heterocyclic carboxylic acid ester from the organic phase and the α-substituted heterocyclic carboxylic acid from the aqueous phase, respectively.

Signed and Sealed this

Fifteenth Day of April, 2003

JAMES E. ROGAN
*Director of the United States Patent and Trademark Office*